United States Patent
Curtis et al.

[11] Patent Number: 5,911,228
[45] Date of Patent: *Jun. 15, 1999

[54] INGREDIENT FILLED POLYTETRAFLUOROETHYLENE DENTAL FLOSS DEVOID TO GRIP ENHANCING COATING

[75] Inventors: John Curtis, Bloomsbury; Karen DePierro, Piscataway, both of N.J.; David Delgado, Levittown, Pa.

[73] Assignees: Colgate-Palmolive Co., New York, N.Y.; Coltec Industrial Products, Inc., Newtown, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/678,619

[22] Filed: Jul. 10, 1996

[51] Int. Cl.⁶ .................................................. A61C 15/04
[52] U.S. Cl. ............................................................ 132/321
[58] Field of Search ...................................... 132/321, 329

[56] References Cited

U.S. PATENT DOCUMENTS

| | | | |
|---|---|---|---|
| 3,699,979 | 10/1972 | Muhler et al. | |
| 4,256,806 | 3/1981 | Snyder | 428/408 |
| 4,776,358 | 10/1988 | Lorch | 132/321 |
| 5,033,488 | 7/1991 | Curtis et al. | 132/321 |
| 5,209,251 | 5/1993 | Curtis et al. | 132/321 |
| 5,220,932 | 6/1993 | Blass | 132/321 |
| 5,518,012 | 5/1996 | Dolan et al. | 132/329 |
| 5,566,691 | 10/1996 | Dolan et al. | 132/321 |

FOREIGN PATENT DOCUMENTS

| | | |
|---|---|---|
| 0358363 | 3/1990 | European Pat. Off. |
| 97/24078 | 7/1997 | WIPO |

*Primary Examiner*—Todd E. Manahan
*Assistant Examiner*—Eduardo C. Robert
*Attorney, Agent, or Firm*—Michael McGreal

[57] ABSTRACT

The floss is comprised of one or more strands of a tensilized polytetrafluoroethylene. The polytetrafluoroethylene is tensilized by stretching with heating to increase the tensile strength and to decrease elongation. The floss is readily grippable since it has an irregular surface. The polytetrafluoroethylene is made to have an irregular surface by having a solid incorporated into the fiber structure. The solid has a diameter of from about submicron size up to about 125% of the thickness diameter of the fiber. The floss will have a coefficient of friction of more than about 0.08. There is an acceptable grippability without the need for a coating. In addition, the solid that is incorporated into the fiber can be a bioactive material for delivery of the bioactive material to the teeth and gums during flossing.

20 Claims, No Drawings

INGREDIENT FILLED POLYTETRAFLUOROETHYLENE DENTAL FLOSS DEVOID TO GRIP ENHANCING COATING

FIELD OF THE INVENTION

This invention relates to a polytetrafluoroethylene dental floss that is grippable without the use of any coatings. More particularly, this invention relates to a polytetrafluoroethylene dental floss where there is an inorganic or organic solid incorporated into the fiber structure to produce an irregular grippable surface on the fiber.

BACKGROUND OF THE INVENTION

Polytetrafluoroethylene fibers have been found to be useful as a dental floss. A particularly useful polytetrafluoroethylene fiber is one that has been termed to be expanded. In U.S. Pat. No. 3,664,915, the term expanded is defined as a polytetrafluoroethylene that has a decreased specific gravity. The fiber undergoes processing, which can include heating and stretching, to produce a node and fibril structure in the fiber. Such fibers are useful as flosses, with the fibers of preferred interest being these fibers which have a tensile strength such that the fiber will not break during flossing, and in addition, where the fiber undergoes substantially no elongation during use as a floss. A stretched polytetrafluoroethylene fiber having these latter properties is preferred as a floss.

The use of polytetrafluoroethylene as a floss is discussed in U.S. Pat. No. 4,776,358. In that patent, there is discussed a floss consisting of a dentifrice between two layers of polytetrafluoroethylene. One problem with this floss is that it is not grippable. The floss material slips through a person's fingers. One solution to this problem was found in U.S. Pat. No. 5,033,488 and U.S. Pat. No. 5,209,251. This was to put a friction increasing coating onto the surface of the polytetrafluoroethylene fiber. The preferred coating is a wax, and in particular a microcrystalline wax. Other coating materials that would adhere to the polytetrafluoroethylene surface and that would increase the coefficient of friction are also described to be useful. These are useful flosses since they are grippable and shred resistant. However, they have some disadvantages.

One disadvantage is that some dental practitioners advise against using a coated floss and in particular a wax coated floss. There is a belief among such practitioners that this results in a wax build-up on a person's teeth. Another disadvantage is that this requires an additional manufacturing step. After the stretched polytetrafluoroethylene fiber is produced, it must be coated. There is the increased cost of a coating material and the coating procedure. The present floss does not have these disadvantages. It provides all of the benefits of a polytetrafluoroethylene fiber of being shred resistant and easily insertable into close inter dental spaces without these disadvantages. It solves the problem of a grippable polytetrafluoroethylene fiber that does not have a coating. This is accomplished by the structure of the fiber itself.

BRIEF SUMMARY OF THE INVENTION

It has been discovered that a polytetrafluoroethylene fiber, including a stretched polytetrafluoroethylene fiber, can be made grippable without the use of a surface coating by the incorporation of a solid material into the structure of the polytetrafluoroethylene fiber. The solid can be an organic or inorganic solid. The function of the solid is to affect the surface energy of the fiber such as by producing an irregular surface on the polytetrafluoroethylene fiber which makes the fiber more grippable. The solids should be sufficient to create an irregular surface on the fiber. In order to produce this irregular surface, the solid particles should have a size of from submicron to more than about 75% of the thickness of the fiber, and even more than about the thickness of the fiber. In a more preferred mode, the size of the solids should be from about submicron to about 125% of the thickness of the polytetrafluoroethylene fiber. The content of solids will depend on many factors such as particle size, particle shape and particle surface area. This will range from about 1 percent by weight to a content where the fiber does not have a sufficient tensile strength to be used as a floss. Preferably, the solids content will range from about 1 percent to about 30 percent by weight.

The net result is a grippable polytetrafluoroethylene fiber. The fiber for use as a floss will have a denier of about 100 to 3,000, and preferably about 600 to 2,400 denier. The thickness will be from about 0.015 mm to about 0.1 mm, and preferably about 0.020 mm to about 0.08 mm. The width will be about 1 mm to about 5 mm, and preferably about 1.5 mm to about 4 mm. The floss can consist of a single fiber on a plurality of fibers. If comprised of a plurality of fibers, these usually will be in a twisted arrangement.

The useful inorganic solids include oxides, fluorides, carbonates, bicarbonates, sulfates, phosphates, pyrophosphates, and mixtures of these materials. Any inorganic solid can be used that will retain its structure during incorporation into the polytetrafluoroethylene material and the processing of the polytetrafluoroethylene material to increase its tensile strength and to decrease its tendency to elongate. The useful organic solids include polymer materials that will retain their shape during the processing of the polytetrafluoroethylene. They must be stable to the physical processing and to the temperatures. Useful organic materials include polytetrafluoroethylene, nylons, aramides, polyesters, phenolics, and other physically and thermally stable polymers. Mixtures of the inorganic solids and organic solids also can be used.

The solids in a preferred embodiment are those that will deliver an active to the teeth and/or gums. Such actives include fluorides such as sodium fluoride, stannous fluoride and monofluorophosphate, phosphates such as alkali and alkaline earth pyrophosphates, astringents such as allantoin and zinc sulfate, coagulants such as iron salts, zinc salts, alum and calcium alginate. Actives and flavors that cannot be incorporated into the fiber can still be coated onto the fiber and delivered to the teeth and/or gums. When an active can be incorporated into the fiber the step of coating the active onto the fiber can be eliminated. Also when incorporated into the fiber the active is more effectively held by the fiber than when the active is coated onto the fiber. It cannot be rubbed off while manipulating the fiber.

During flossing, a length of about 46 cm of the floss of the present invention is cut from a spool, wrapped around a finger on each hand, and then inserted between teeth to remove food debris and plaque. The floss does not slip from the fingers with the grip being maintained. In addition, the floss does not shred or break during use. The floss, although an uncoated polytetrafluoroethylene, is easily gripped.

DETAILED DESCRIPTION OF THE INVENTION

It has been found that non-coated polytetrafluoroethylene fibers can be used as a dental floss. The problem with regard to the use of polytetrafluoroethylene fibers as flosses is that the property that makes them useful as a floss, that is their lubricity, also is a disadvantage. These fibers due to their inherent lubricity can be easily inserted between a person's teeth, even in close inter dental spaces. However, this same property of lubricity makes the fiber difficult to grip. It has been found that the lubricity of the fiber for flossing can be retained, but the lubricity can be decreased sufficiently to make it grippable.

The technique to make the fiber grippable consists of adding a solid to the fiber as the fiber is being produced. The solid can be an inorganic or organic solid. The useful inorganic solids include oxides such as silicas, aluminas, titanias, and aluminosilicates, fluorides, such as sodium fluoride, stannous fluoride and monofluorophosphate, carbonates such as sodium carbonate, potassium carbonate, calcium carbonate and magnesium carbonate, bicarbonates such as sodium bicarbonate and potassium bicarbonate, sulfates such as sodium sulfate and potassium sulfate, phosphates and pyrophosphates such as sodium phosphates, potassium phosphates, sodium pyrophosphate and potassium pyrophosphate and mixtures of these solids. The useful organics include particulate polytetrafluoroethylene, nylons, aramides, polyesters, phenolics, and other physically and thermally stable polymers. Mixtures of organic and inorganic solids also can be used.

Preferred solids to be incorporated into the fibers are solids that also are bioactives. By bioactives it is meant solids that will deliver a substance that has some medicant effect on the teeth and/or gums. These include fluorides such as sodium fluoride, stannous fluoride and monofluorophosphate, pyrophosphates such as sodium and potassium pyrophosphate, astringents such as allantoin and zinc sulfate and coagulants such as iron salts, zinc salts, alum and calcium alginate. Bioactives that cannot be incorporated into the fiber can be coated onto the fibers. Flavors are preferably in a spray dried form when incorporated into or applied onto the floss fiber or fibers. Liquid bioactives and flavors can be in an encapsulated form or can adsorbed into solids such as silicas, aluminas and aluminosilicates. These can be incorporated into or coated onto the fibers. When the bioactive is in a coated form the coating is applied to the fiber or fibers from a viscous polymeric solution. A useful polymer solution is one that contains polyvinyl alcohol or polyvinyl acetate along with water and a glycol such as polyethylene glycol. This is coated onto the fiber or fibers and the coating dried.

The solids will have a particle size of from submicron to greater than the thickness of the fiber. An objective is to lower the surface energy of the fibers to near that of the solids and to thereby make the fibers more grippable. This is accomplished by the incorporating of solid particles into the fiber in order to have an affect on the surface of the fiber. Smaller particle sized particles can be used where at a particular loading or in a particular size, shape or form the solid will have an impact on the fiber surface. The particles can be approximately spherical to elongated to irregular. They can have a high or low surface area. Further, the solid particles can have a near constant particle size or can have a range of particle sizes. The particle packing will have an affect. Small particle size solids with high surface areas can be very useful. These will tend to affect the fiber surface more than other solids. A limiting factor with regard to the particular solid will be the affect on fiber strength as the loading is increased. In general, as the content of the solid is increased, the strength of the fiber will decrease. Consequently, since the floss will need a sufficient tensile strength to withstand abrasive movements over teeth when used as a floss, there is a practical limit on the amount of solids that can be put into the fiber.

With all of these considerations, there can be some generalizations. The solids can have a particle size in the range of from submicron to about 125 percent of the thickness of the fiber. The particles usually will be irregular in shape and have an average particle size within this range. The surface area can range from essentially only the exterior surface to several hundred square meters per gram for solids with high interior surface areas. Silicas and aluminas can typically have surface areas in the range of several hundred meters per grams.

The surface energy of polytetrafluoroethylene is in the range of 21 dynes/cm$^2$. Various solids have higher surface energies and when at or adjacent to the polytetrafluoroethylene fiber surface will raise the surface energy of the fiber. The net result will be a more grippable polytetrafluoroethylene floss due to the resultant higher surface energy.

The solids also can be bioactive materials. Useful bioactive materials include fluorides such as sodium fluoride, stannous fluoride and monoflurophosphate, phosphates such as alkali and alkaline earth pyrophosphates, astringents such as allantoin and zinc sulfates, coagulants such as iron salts, zinc salts, alum and calcium alginate. Bioactives that cannot be incorporated into the fiber can be coated onto the fibers and delivered to the teeth and gums. Additionally, the bioactives that are incorporated into the fiber also can be coated into the fiber in order to provide a higher dose of the bioactive upon the start of flossing. This is a useful technique since it will take a period of time to lead the solid bioactive from within the fiber and then to deposit this bioactive onto a person's teeth and gums. The leach rate will be slow on the start of flossing and increase during flossing.

The amount of loading of solids into the fiber will range from about 1% by weight to an amount where the fiber loses an effective tensile strength. As the loading of the solids increases the tensile strength will decrease. Loadings up to the point where the fiber breaks during flossing can be used. However, the amount incorporated will be less than the break point and will be in the range of effective gripping. The amount of loading will depend on the particular solid, its average particle size, particle shape surface area and surface energy among other factors. Depending on these factors the loading can range up to about 30% by weight.

The fiber will have a denier of about 100 to 3,000 and preferably about 400 to 2,400. The thickness of the fiber will be about 0.015 mm to about 0.1 mm, and preferably about 0.020mm to about 0.08 mm. The width is about 1 mm to about 5 mm, and preferably about 1.5 mm to about 5 mm. The floss can be a single fiber or comprised of a plurality of polytetrafluoroethylene fibers. If a plurality of fibers, they preferably will be in an arrangement with about 3 to 10 twists per inch.

The polytetrafluoroethylene is one that has sufficient tensile strength that it will not break during flossing. In addition, it will have substantially no elongation during use as a floss. By substantially no elongation, it is meant that there will be less than about 10%, and preferably less than about 5% elongation during flossing conditions. The fiber usually is produced from a polytetrafluoroethylene powder. The polytetrafluoroethylene powder, the solid and a lubricant are mixed together, and the mixture extruded into a sheet of polytetrafluoroethylene. The sheet then is processed with stretching and heating to increase the tensile strength of the sheet and to reduce the degree of elongation of the sheet in subsequent use. The stretching can be a uniaxial or biaxial stretching. During a uniaxial stretching, the sheet will increase in length while substantially maintaining the thickness and width of the sheet. The specific gravity of the sheet will decrease during the stretching and heating processing. This is the result of sheet developing a node and fibril internal structure which results in an increased tensile strength. Various types of these stretched polytetrafluoroethylenes are known also as expanded polytetrafluoroethylenes.

Techniques for producing useful polytetrafluoroethylene sheets is described in any of U.S. Pat. No. 3,664,915, U.S. Pat. No. 3,953,566, and U.S. Pat. No. 4,096,227. These patents broadly describe how to produce a polytetrafluoroethylene that has a sufficient tensile strength and an acceptable degree of elongation during flossing. A most preferred tensile strength is about 7,000 psi or more, and preferably about 10,000 psi to about 75,000 psi. Most preferably, it is about 20,000 psi to about 50,000 psi. The polytetrafluoroethylene materials in these patents are described as expanded polytetrafluoroethylenes.

The coefficient of friction of polytetrafluoroethylene is about 0.06. This is the coefficient of friction of an unfilled and uncoated polytetrafluoroethylene. In order to be easily grippable, the coefficient of friction should be greater than about 0.08, and preferably greater than about 0.12. The prior art wax coated polytetrafluoroethylene flosses have a coefficient of friction greater than about 0.12. The present solid containing polytetrafluoroethylene usually will have a coefficient of friction of greater than about 0.12.

A useful technique for making the present polytetrafluoroethylene is to mix a polytetrafluoroethylene powder, the solid, and a hydrocarbon lubricant into a consistency of a dough. This dough is then extruded into a sheet and is calendered to the desired thickness. The extrusion is at a temperature of well below the melting temperature of the polytetrafluoroethylene. After extrusion and calendering, the polytetrafluoroethylene sheet is rapidly stretched to about 1.5 to about 10 times its original length, and preferably to about 2 to about 6 times its original length. This produces a node and fibril structure in the interior of the polytetrafluoroethylene. This stretched polytetrafluoroethylene also can be termed an expanded polytetrafluoroethylene. This sheet of stretched polytetrafluoroethylene then is cut into fibers having the desired width. One useful width is about 2.5 mm which in a fiber 5 having a thickness of about 0.030 mm is nominally a 1,200 denier fiber. These fibers then are placed onto small spools for subsequent use as a dental floss.

The fibers also can be cut from the polytetrafluoroethylene sheet to a width of less than 2.5 mm to produce a 600 or 800 denier floss or a multi-filament floss and to a width of more than 2.5 mm to produce a tape type of floss. When in a multi-filament form the fibers usually will be twisted together in a form of about 3 to 10 twists per inch and collected on a spool. These are useful floss variants and can be used as is or coated with one or more bioactives. In addition, any of the floss variants of this invention can be coated with one or more flavors. Usually, this will be a coating of a spray dried flavor. A useful coating technique is disclosed above.

EXAMPLE

This example illustrates that when sodium fluoride is the solid that is incorporated into the floss fiber that the fluoride is available from the floss onto the teeth and gums that it contacts.

An expanded polytetrafluoroethylene floss is produced having loadings of sodium fluoride of 10.7 percent by weight, 7.5 percent by weight and 3.75 percent by weight. The floss has a nominal thickness of 0.068 mm and a width of 2.6 mm. The floss is cut into lengths of 46 cm and placed in 10 ml. of distilled water at about 26° C. for 10 minutes. The floss is then removed and the water analyzed for ionic fluoride. The amount of ionic fluoride that is leached from each sample is given in Table 1.

TABLE 1

| Floss Length | Floss NaF % | F⁻ Content of HOH |
| --- | --- | --- |
| 46 cm | 10.7 | 11.3 mg |
| 46 cm | 7.5 | 4 mg |
| 46 cm | 3.75 | 3.6 mg |

An effective delivery of fluoride to a persons teeth is considered to be about 0.15 mg per 46 cm of floss. It is seen that a sodium fluoride containing polytetrafluoroethylene will effectively deliver fluoride to a persons teeth. This is in addition to making the floss more grippable.

This invention has been described in its preferred embodiments. In the broad sense the invention comprises use of solids within polytetrafluoroethylene fibers to increase the coefficient of friction so that the fiber can be readily gripped and used as a floss.

We claim:

1. A dental floss comprising at least one polytetrafluoroethylene fiber having a denier of about 100 to 3,000, said fiber devoid of any grip enhancing coating to make the fiber grippable, having a tensile strength sufficient to resist breaking during insertion between interdental spaces and no substantial elongation during use as a floss, containing a solid additive within its structure sufficient to provide a surface energy of more than 21 dynes/cm$^2$ and a coefficient of friction of more than about 0.08, said solid additive having a diameter of up to about 125% of the thickness of said fiber whereby said fiber has an irregular surface that makes said fiber readily grippable for use as a dental floss.

2. A dental floss as in claim 1 wherein said solid additive has a diameter of up to about the thickness of said polytetrafluoroethylene fiber.

3. A dental floss as in claim 1 wherein said solid additive decreases the tensile strength of said polytetrafluoroethylene fiber and is present in an amount of up to the breaking point of said polytetrafluoroethylene fiber during use as a floss.

4. A dental floss as in claim 1 wherein said solid additive is in a content of about 1 percent to 30 percent by weight.

5. A dental floss as in claim 1 wherein said solid additive is an inorganic solid.

6. A dental floss as in claim 5 wherein said inorganic solid is selected from the group consisting of oxides, fluorides, carbonates, bicarbonates, phosphates, pyrophosphates and mixtures thereof.

7. A dental floss as in claim 6 wherein said inorganic solid is sodium fluoride.

8. A dental floss as in claim 1 wherein said solid additive is an organic solid.

9. A dental floss as in claim 8 wherein said organic solid is selected from the group consisting of polytetrafluoroethylene, nylons, aramides, polyester, phenolics and mixtures thereof.

10. A dental floss as in claim 1 wherein said solid additive is a bioactive material.

11. A dental floss as in claim 10 wherein said bioactive is sodium fluoride.

12. A dental floss as in claim 1 wherein said polytetrafluoroethylene fiber has a thickness of about 0.015 mm to about 0.1 mm and a width of from about 1 mm to about 5 mm.

13. A dental floss as in claim 12 wherein said polytetrafluoroethylene fiber has a thickness of about 0.020 mm to about 0.08 mm and a width of from about 1.5 mm to about 4 mm.

14. A method of flossing teeth comprising gripping a length of a dental floss, selecting of at least one polytetrafluoroethylene fiber having a solid dispersed therein, a surface energy of more than 21 dynes/cm$^2$ and a coefficient of friction of more than about 0.08, said fiber devoid of any grip enhancing coating, inserting said dental floss in a space between teeth, and moving said dental floss within said space between teeth to remove material form said teeth.

15. A method as in claim 14 wherein said solid is selected from the group consisting of inorganic solids, organic solids and mixtures thereof.

16. A method as in claim 15 wherein said solid is a bioactive material.

17. A method as in claim 16 wherein said bioactive is sodium fluoride.

18. A method as in claim 14 wherein said solid is present in a content of about 1 to about 30 percent by weight.

19. A method as in claim 14 wherein said solid has an average particle size of from about submicron size to about 125% of the thickness of said fiber.

20. A method as in claim 14 wherein said floss has a coefficient of friction of at least about 0.12.

* * * * *